United States Patent
Jansen et al.

(10) Patent No.: US 7,302,355 B2
(45) Date of Patent: Nov. 27, 2007

(54) METHOD AND APPARATUS FOR CALIBRATING CIRCULAR OBJECTS USING A COMPUTER TRACKING SYSTEM

(75) Inventors: Herbert André Jansen, Montréal (CA); Pierre Couture, Montréal (CA)

(73) Assignee: Orthosoft Inc., Montréal, Québec (CA)

( * ) Notice: Subject to any disclaimer, the term of this patent is extended or adjusted under 35 U.S.C. 154(b) by 0 days.

(21) Appl. No.: 11/434,787

(22) Filed: May 17, 2006

(65) Prior Publication Data

US 2006/0265179 A1    Nov. 23, 2006

Related U.S. Application Data

(60) Provisional application No. 60/682,872, filed on May 20, 2005.

(51) Int. Cl.
*G01P 21/00* (2006.01)
*G06F 19/00* (2006.01)
*G01C 17/38* (2006.01)

(52) U.S. Cl. .................. 702/95; 600/427; 606/130; 73/1.79; 73/1.81; 702/107

(58) Field of Classification Search ............ 702/94, 702/95, 150–153, 155, 157; 600/424, 426, 600/427; 606/1, 130; 73/1.79, 1.81
See application file for complete search history.

(56) References Cited

U.S. PATENT DOCUMENTS

| 5,987,960 | A | 11/1999 | Messner et al. |
| 6,190,395 | B1 * | 2/2001 | Williams .................... 606/130 |
| 6,697,664 | B2 * | 2/2004 | Kienzle III et al. ......... 600/427 |

FOREIGN PATENT DOCUMENTS

WO    02061371    8/2002

OTHER PUBLICATIONS

International Search Report of PCT application No. PCT/CA2006/000815.

* cited by examiner

*Primary Examiner*—John Barlow
*Assistant Examiner*—John Le
(74) *Attorney, Agent, or Firm*—Ogilvy Renault LLP (57) ABSTRACT

A method of calibrating a circular portion of an object, such as to determine the center point of the object, is provided. The method includes determining spatial coordinates of at least two points on a circumferential edge of the circular portion of the object, and calculating the center point of the circular portion using the spatial coordinates of the two points and a geometric parameter representative of the diameter of the circular portion. A calibration device and system are also provided for use with a computer tracking system in order to calibrate such an object having a circular portion.

27 Claims, 8 Drawing Sheets

METHOD AND APPARATUS FOR CALIBRATING CIRCULAR OBJECTS USING A COMPUTER TRACKING SYSTEM

CROSS-REFERENCE TO RELATED APPLICATIONS

This application claims priority on U.S. Provisional Patent Application Ser. No. 60/682,872 filed May 20, 2005, the entire contents of which is incorporated herein by reference.

TECHNICAL FIELD

The invention relates generally to calibrating a calibration device and method for use with a computer tracking system, such as a computer assisted surgery system for example, and more particularly to an improved method and apparatus for determining at least the center of a circular object.

BACKGROUND OF THE ART

Proper calibration of tools, implants and other components used in computer assisted surgery (CAS) procedures is vital.

Several CAS procedures require the determination of the center of rotation of a circular object, a cup or a half-sphere. For example, total hip replacement (THR) procedures require that the acetabular cup implant be properly calibrated such that the CAS system accurately knows the exact location in space of the center of the cup, which is typically held by an impactor tool having a handle defining an axis through which the center of rotation of the cup is concentric.

Several techniques are currently employed to determine the center of prosthetic cups and other hemispherical shaped objects used in CAS procedures. One common technique involves immobilizing the cup in question in a reference block and subsequently employing a digitizing CAS pointer to determine individually and sequentially at least three points along the outer circumference of the cup's rim. The CAS system then calculates the corresponding center of the circular cup based on three known points acquired on its circumference. While generally effective, several disadvantages exist with this procedure and the associated equipment required. For example, the need for a relatively large reference block capable of immobilizing the cup and the time required to digitize the individual points on the cup are both disadvantages for which improvement is sought. Further, the associated handling error which can result from digitizing points on the object retained within the reference block can cause differences between the calculated center determined by the CAS system and the true center of the circumference. These differences, while sometimes small, can be significant enough to considerably affect the results.

SUMMARY OF THE INVENTION

It is therefore an object of this invention to provide an improved method and apparatus for determining at least the center of a circular object.

In one aspect, the present invention provides a method of determining a center point of a circular portion of an object, the circular portion having a diameter, the method comprising the steps of: determining spatial coordinates of at least two points on a circumferential edge of said circular portion of the object; and calculating the center point of said circular portion using said spatial coordinates of said at least two points and a geometric parameter representative of the diameter of said circular portion.

In another aspect, the present invention provides a method of calibrating an object having at least a circular portion defining a diameter for use with a computer tracking system, the method comprising: providing a calibration device having thereon a tracking member which is located and tracked in three dimensional space by the computer assisted tracking system, the calibration device including at least two object contacting portions located known distances from said tracking member and apart from each other; abutting said at least two object contacting portions against a circumferential edge of said circular portion such that said at least two object contacting portions contact said circumferential edge at two points thereon; using the computer tracking system to determine spatial coordinates of said two points on said circumferential edge of the circular portion; and calculating a center point of said circular portion using said two points on said circumferential edge and a geometric parameter representative of the diameter of the circular portion.

In another aspect, the present invention provides a system for calibrating an object having a circular portion, the system comprising: a computer tracking system operable to locate and track in three dimensional space a plurality of tracking members communicable with the computers tracking system; a calibration device including at least one of said tracking members thereon, the calibration device having at least one object receiving surface thereon for abutment with at least the circular portion of the object; and a calculation algorithm defined stored within the computer tracking system, said calculation algorithm being operable to calculate at least one of spatial coordinates of a center point of the circular portion and a geometric parameter of the circular portion representative of a diameter thereof.

There is also provided, in accordance with another aspect of the present invention, a calibration device for calibrating at least a circular portion of an object using a computer tracking system, the circular portion having at least a curved circumferential edge and an intersecting planar face, the calibration device comprising: a main body having a platform portion defining at least a first planar surface thereon, the first planar surface being adapted for receiving the planar face of the circular portion abutted there against, and at least two elements projecting from said first planar surface, said elements being spaced apart such as to receive the curved circumferential edge of the circular portion therebetween when said curved circumferential edge is abutted against said elements; a tracking member fixed to said main body, the tracking member being locatable and trackable in three dimensional space by the computer tracking system; and said first planar surface and each of the elements being located a known distance from said tracking member such that their position and orientation in three dimensional space is determinable by the computer tracking system, and thus the spatial coordinates of points on the curved circumferential edge and the planar face of the circular portion which are abutted against said first planar surface and said elements are accordingly determinable by the computer tracking system.

Further details of these and other aspects of the present invention will be apparent from the detailed description and figures included below.

DESCRIPTION OF THE DRAWINGS

Reference is now made to the accompanying figures depicting aspects of the present invention, in which:

FIG. 2b is a schematic top plan view of the calibration device and the object of FIG. 2a;

DETAILED DESCRIPTION OF THE PREFERRED EMBODIMENTS

Computer tracking systems, such as computer assisted surgery (CAS) systems for example, which are capable of real time location and tracking of a plurality of discrete objects in space are now becoming increasingly employed in a number of different fields. For example only, the use of CAS systems by surgeons, particularly in the orthopedic field, is become more common. A variety of such computer tracking systems are used, however most require the tracked object, such as a patient bone or a surgical tool for CAS systems, to be identified and registered to predetermined images of the object in question, for example registered to pre-operatively taken anatomical scans or intraoperatively taken images of the same bone elements. Therefore, by using trackable members which can be located and tracked in space by the computer tracking system, the operator of the computer tracking system is able to use the system as an aid when conducting procedures on or using the given object. Further, all tools employed when conducting such procedures must typically also be identified and tracked by the system in real time relative to the position of the other tracked objects. In order to ensure accuracy and repeatability, all tracked tools, objects, implants, and the like employed in conjunction with such a computer tracking system must therefore be precisely calibrated. The term "computer tracking system" as used herein is defined as including any computer based system which is used for sensing the position and orientation of a tracked object in three dimensional space. This can include, but is not limited to, a CAS systems for example. Any suitable computer assisted tracking and/or guidance system is thus possible. Although the computer tracking system of the present invention will be generally described hereinbelow with reference to a CAS system embodiment, it is thus understood that the computer tracking system of the present invention is not limited to such a surgical application.

Figure 1A:
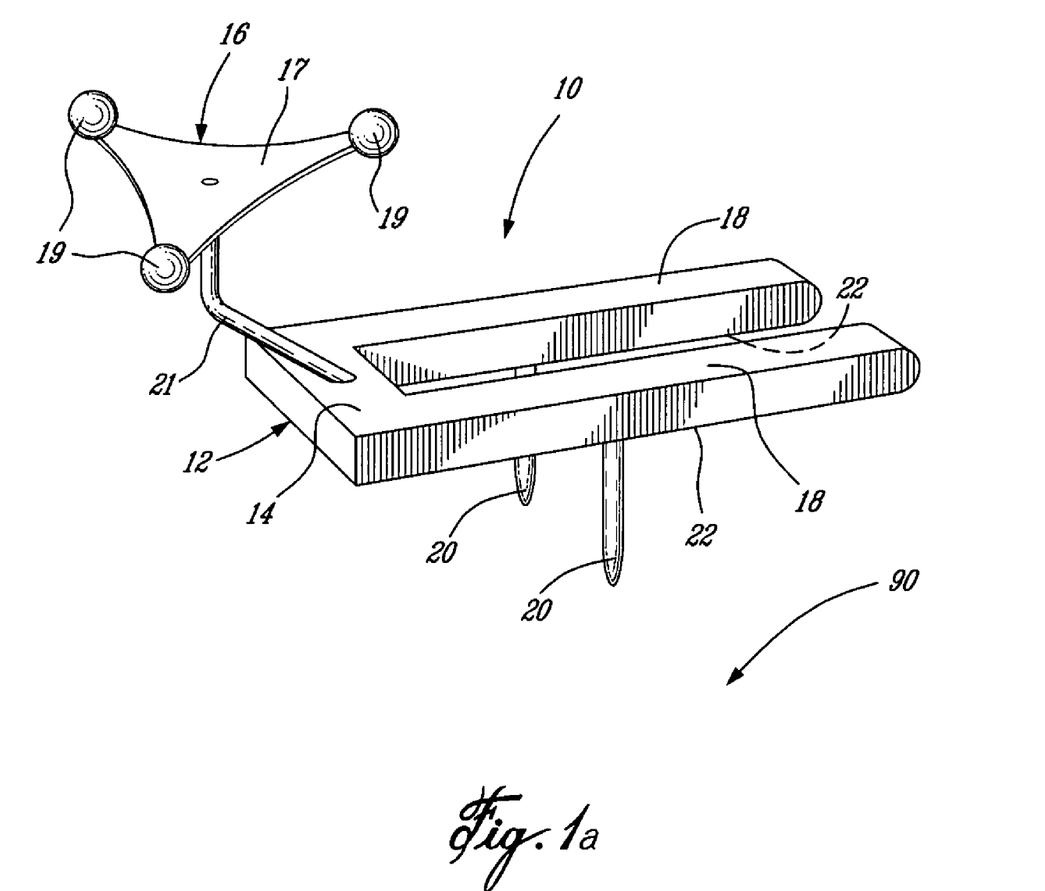
FIG. 1a is schematic perspective view of a calibration device in accordance with one embodiment of the present invention.
Figure 1B:
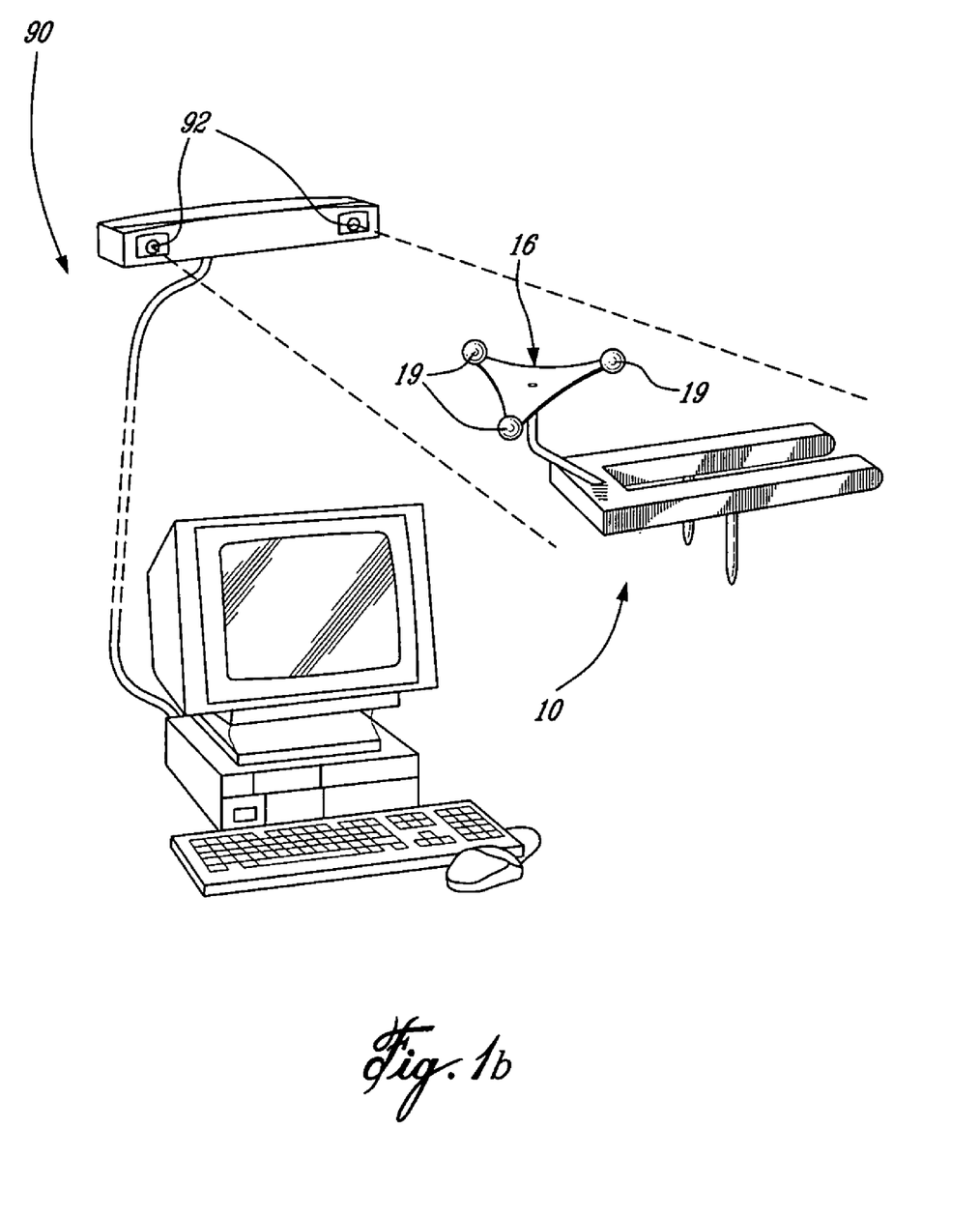
FIG. 1b is a schematic perspective view of the calibration device of FIG. 1a and a computer tracking system for use therewith.

The calibration device 10 of the present invention is particularly adapted to be used with such a CAS system 90, such as that schematically depicted in FIG. 1b, in order to calibrate a surgical object to be used in a CAS procedure, and more particularly a circular surgical object.

The term "circular portion" is used herein to define any circular-shaped portion of an object which defines a curved outer surface having a center point. Such objects may include spherical, hemispherical, cup-shaped, planar circular objects and other objects which have a circular perimeter (i.e. a circumference) and/or have at least a portion defining a circular cross-section. The terms "circular object" or "circular portion" is used herein interchangeably to include all such objects. For example, prosthetic acetabular cups used in hip replacement surgery, and other circular objects used in orthopedic surgery, either as part of a tool or a prosthetic device. The centers of such circular objects may also correspond to their axis of rotation about this center point, thus the present invention permits such an axis of rotation to be similarly determined, along with the centers of the circular objects calibrated using the device and method of the present invention. The term "surgical object" as used herein is defined as comprising any surgical tool, implant or other object which is or can be used in a surgical environment, for either CAS or non-CAS based surgical procedures.

Figure 2A:
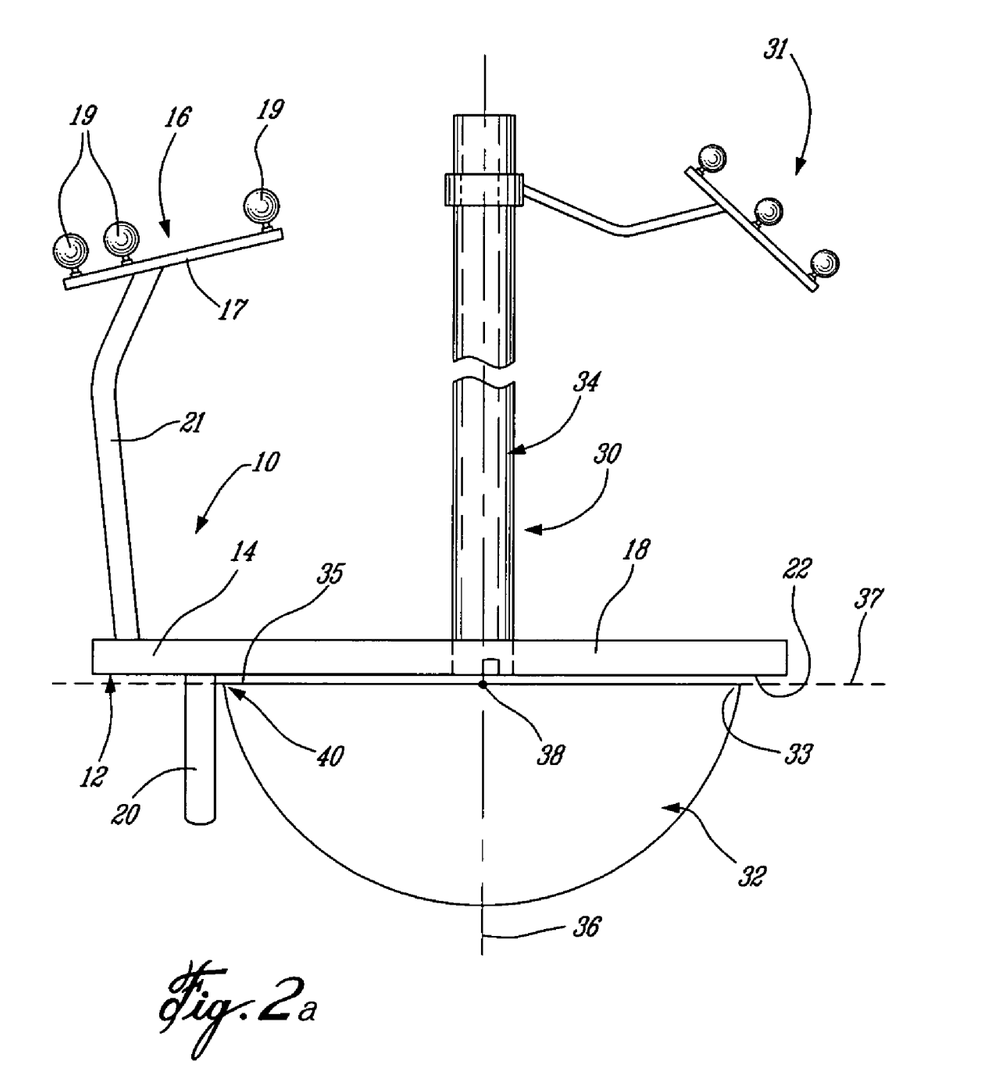
FIG. 2a is a schematic side elevation view of the calibration device of FIG. 1 in use to determine a center of a hemispherical object.

Referring now to FIGS. 1a-1b, the calibration device 10 is preferably a relatively small, hand held CAS calibrator which permits the instant determination of a circular object's center, which is typically a center of rotation thereof about a perpendicularly extending axis, and the plane within which the center point lies. The calibration device 10 comprises a main body 12 defining a U-shaped platform including a central portion 14 interconnecting a pair of legs 18 which are spaced apart from each other and extend from the central portion 14, thereby forming the generally U-shaped platform of the main body 12. The lower surfaces 22 of the legs 18 are planar such that they may be overlaid and abutted flat against a planar surface 35 of the circular object 32, as best seen in FIG. 2a. The planar surface 35 of the circular object 32 being calibrated using the device 10 is substantially perpendicular to an axis of rotation 36 extending therethrough. The planar surface 35 of the hemispherical cup 32 defines a plane 37 within which it lies. As the position in space of the lower surfaces 22 of the legs 18 are known by the CAS system 90 tracking the calibration device 10, the CAS system is thus able to identify and calibrate the position and orientation of the plane 37 defining the planar circumferential surface 35 of the hemispherical cup 32.

A projection 20, such as a pin or prong for example, extends preferably perpendicularly, from the planar surfaces 22 of each of the legs 18. By virtue of being disposed on each leg 18, the projections 20 are therefore spaced apart and are thus adapted to receive a circumferential edge of the circular object therebetween. These projections 20 can therefore be abutted against the circumferential edge 33 of the circular object 32 for which the center is to be determined, as described in further detail below and depicted in FIGS. 2a-2b. The projections 20 are disposed in a determinable location on the calibration device 10 relative to a tracking member 16 fixed thereto. Although preferably the projections 20 are fixed in place and immovable relative to the legs 18 and the rest of the main body 12, it remains possible that they are displaceable, such as to accept circular objects of varying sizes for example, providing that the relative position between the tracking member 16 and the projections is known or can be determined by the CAS system 90 (FIG. 1b) or is identified thereto manually by a user.

The tracking member 16, which is located and tracked in three dimensional space by the CAS system 90 (as depicted in FIG. 1b) used in conjunction with the calibration device 10, is preferably permanently fixed to the main body 12 of the calibration device 10. The tracking member 16 generally comprises a tracker head element 17, preferably having three detectable elements (i.e. CAS identification markers) 19 disposed, and preferably removably engageable from the head element 17. The detectable tracker head element 17 is engaged to the main body portion 12 by the fixed support rod 21. Each identification marker or detectable element 19 is, in at least one embodiment, an optically detectable sphere. The detectable spheres 19 are preferably coated with a retro-reflective layer in order to be detected by, for example, at least two cameras and/or infrared sensors 92 (FIG. 1*b*) of the CAS system. Cameras of the optical CAS system can therefore detect the position of each optically detectable sphere 19 illuminated by infrared light. Each detectable marker element 19 can alternately be any other type of position indicator such as a light emitting diode (LED) or a detectable electromagnetic indicator, provided each can be detected by the type of sensor used by the specific CAS system. Although the present calibration device 10 is most preferably adapted for use with an optically based CAS system 90 (FIG. 1*b*), one skilled in the art will appreciate that in addition to the optical system mentioned above, other types of CAS tracking systems can equivalently be used, such as, for example, those which use electromagnetic, ultrasound or laser as a means for position identification. In such cases, it is to be understood that the detectable marker elements 19 will be such that they are able to indicate to, and/or be detected by, the particular CAS position identification system used. Thus, for an optical CAS system, the trackable reference member comprises at least three optically detectable markers 19 whose exact position and orientation can be determined by each of the at least two cameras 92 of the optical CAS system 90 (FIG. 1*b*), thereby permitting the exact position and orientation in space of each detectable marker to be determined by the CAS system. This permits the CAS system to determine the position and orientation of the calibration device to which the trackable member is fixed.

Figure 2B:
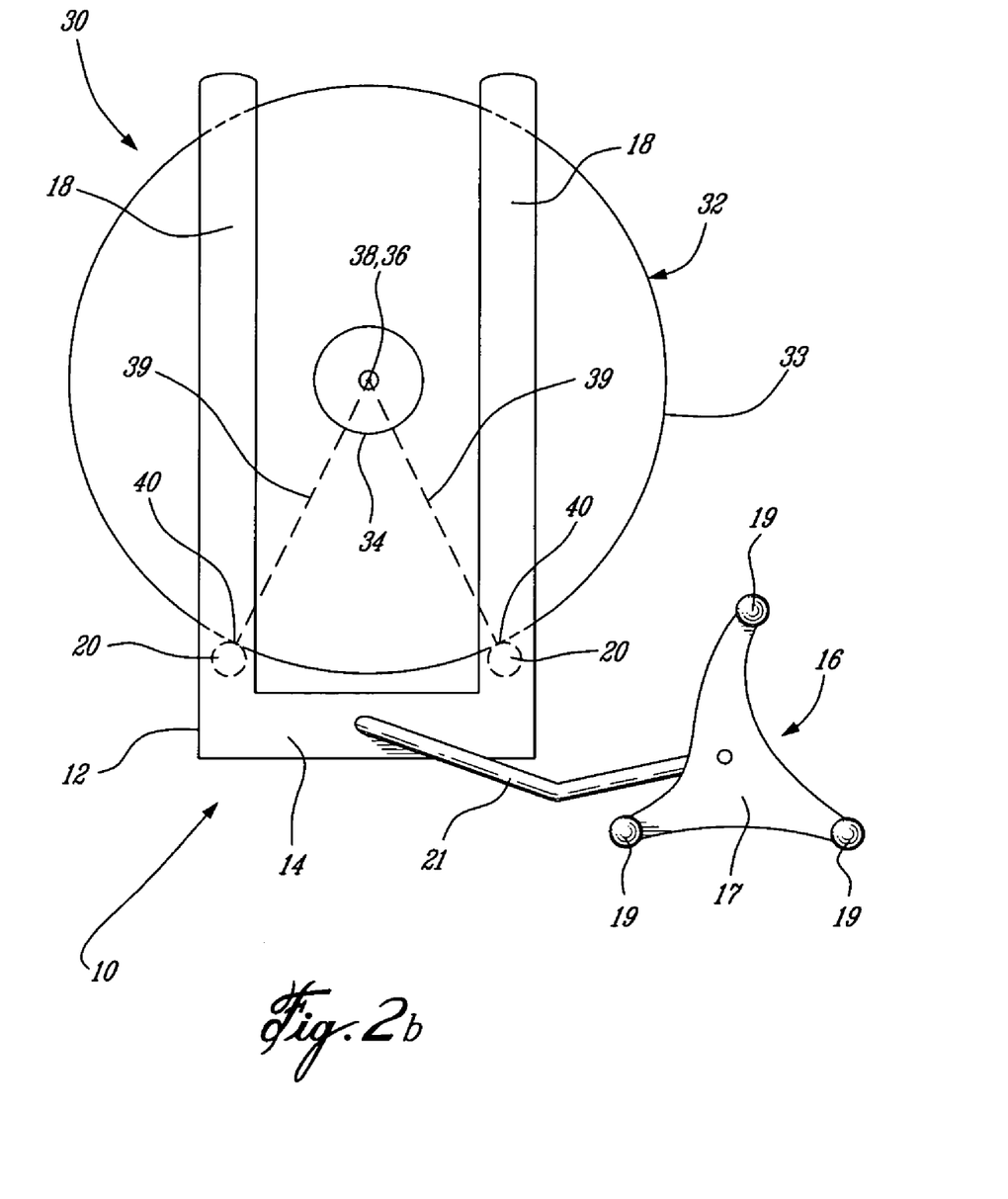

Referring now back to FIG. 2*a*-2*b*, the calibration device 10 is shown in use to calibrate a prosthetic acetabular cup 32 (i.e. a circular surgical object) which is being held by an impactor 30, which is a tool commonly used in total hip replacement surgery. The calibration device 10 permits the determination of the center of the circular edge of the cup and therefore the center of rotation thereof about the perpendicular axis 36 which extends therethrough perpendicularly to the planar surface 35 and therefore the plan 37 it defines. The perpendicular axis 36 of the cup 32 is also coincident with the longitudinal central axis of the impactor shaft 34. The impactor may also have a tracking member 31 engaged thereto such that the CAS system 90 (FIG. 1*b*) is able to locate and track this tool in the surgical field. The hemispherical object 32 may be a hollow cup having a hemispherical outer surface and a hollow interior (as per an acetabular cup), or may alternately be solid. Regardless, the hemispherical cup 32 defines a circumferential rim or edge 33 at its largest point, and a planar surface portion 35 substantially perpendicular thereto. The planar surface 35 defines the plane 37 within which it lies, the plane being orthogonal to the longitudinal axis 36 of the handle 34. The handle or shaft 34 extends from the head 32 co-axially with the central axis 36 which extends through the shaft 34 and the center point 38 of the head 32.

In use, in order to determine the location of the center point 38 of the cup 32, and therefore the axis of rotation 36 as well as the orientation of the plane 37 in the three dimensional space of the surgical field, the calibration device 10 is engaged with the cup 32 as follows. The legs 18 of the main body 12 of the calibration device 10 are placed overtop and abutted against the planar surface 35 of the circular object, in this case the hemispherical cup 32, such that the planar lower surfaces 22 of the legs 18 overlay and rest directly upon the planar surface 35. The legs 18 may be held down manually on the planar surface 35 if necessary. Therefore, once so abutted, the CAS system is able to determine the position and orientation of the plane 37 of the object, by identifying the position and orientation of the surfaces 22 of the legs 18 on the calibration device 10 which are abutted against the planar surface 35 and disposed in a known location relative to the tracking member 16. This step of determining the position and orientation of the plane 37 defined by the object to the calibrated can be either performed initially, or simultaneously with the determination of the center of the circular portion of the object, which lies within this plane, as described below.

Once the legs 18 are abutted against the planar surface 35 of the object, the main body 12 may then be translated along the planar surface 35 until both projecting pins 20 are abutted directly against the circumferential edge 33 of the circular object (as shown in FIGS. 2*a* and 2*b*). Although in this described embodiment the circular object to be calibrated comprises such a planar surface on which the legs 18 of the calibration device 10 may abut, it is to be understood that a calibration device in accordance with the present invention may calibrate circular objects without such a planar reference surface for abutment (such as a full sphere, for example). For such cases, either the pins 20 are the only elements of the calibration device which abut the object, namely about a circumferential edge thereof, or alternately the calibration device provides at least an additional abutting surface which is configured to rest against an outer surface portion of the object when the pins are abutted against the circumferential edge thereof.

Regardless, the pins 20 therefore abut the circumferential edge 33 of the circular object 32 at two contact points 40 thereon. As the location of the pins 20 relative to the tracking member 16 are fixed, or at least known, the CAS system which is locating and tracking the tracking member 16 is therefore able to determine the location in space of the pins 20, and therefore the contact points 40 on the outer circumferential edge 33 of the circular object 32. Accordingly, knowing the spatial coordinates of these points 40 as well as a geometric parameter representative of the diameter of the circular object, the CAS system is able to calculate the exact center point 38 of the circular object, and therefore the coincident central axis of rotation 36 thereof. The term geometric parameter representative of the diameter as used herein is intended to include any geometric measurement of the circular object which is either a function of the diameter or can be used to calculate the diameter. For example, this geometric parameter includes the diameter itself of the circular object, its radius, its circumference, etc. This can be done using any one of a variety of possible algorithms, for example by calculating an intersection point between two imaginary lines 39 (FIG. 2*b*), each line having one of said two contact points at an origin thereof and a length equal to the radius (i.e. half the known outer diameter of the object). The diameter of the circular object may be manually inputted into the CAS system by the user beforehand, or alternately, once the calibration device has been located in place on the circular object to be calibrated, the CAS system may prompt the user, via a suitable interface such as a monitor or the like, to input the known outer diameter or radius of the object. Alternately still, as in the embodiment described below with reference to FIGS. 3 to 5, the calibration device may further be able itself to permit the CAS to automatically determine the diameter of the circular object, (include a diameter determining element) such that this information need not be known in advance. Although the radial dimension of the spherical object used to calculate its center position is generally referred to herein as the diameter of the circular objects, it is to be understood that the radius of the circular object can be similarly used.

Therefore, the calibration device 10 permits the CAS system 90 to quickly and easily determine the center 38 and axis of rotation 36, as well as a reference plane 37 defining a planar surface, of a circular object to be used in conjunction with the CAS system, such as the prosthetic acetabular cup 32 depicted, without having to manually acquire or digitise individual points. Preferably, the reference plane 37 is orthogonal to the axis of rotation 36 and the center point 38 lies within this plane.

Figure 3:
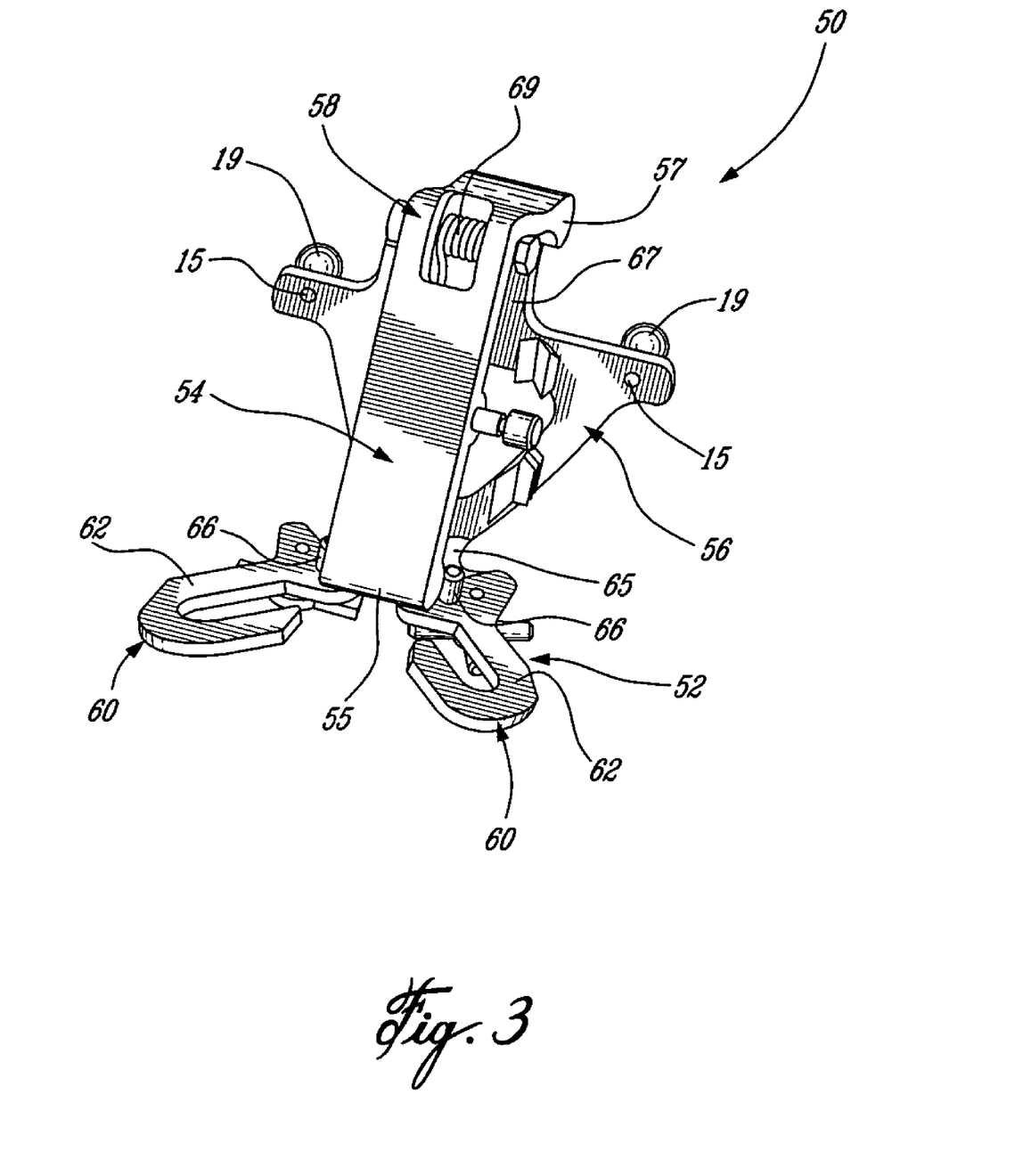
FIG. 3 is a top perspective view of a CAS calibration device in accordance with another embodiment of the present invention.
Figure 4:
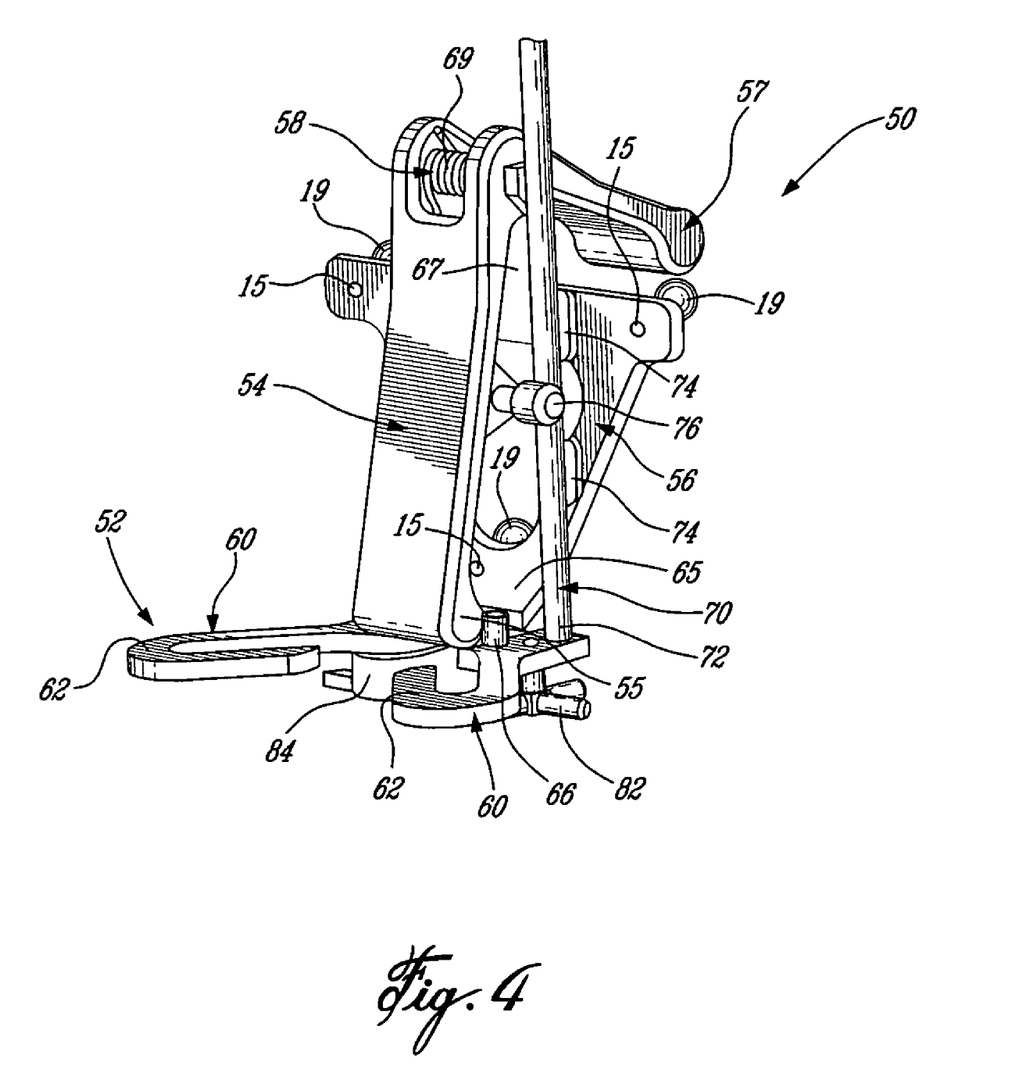
FIG. 4 is a front perspective view of the calibration device of FIG. 3, shown with an additional instrument installed therein for calibration thereof.
Figure 5:
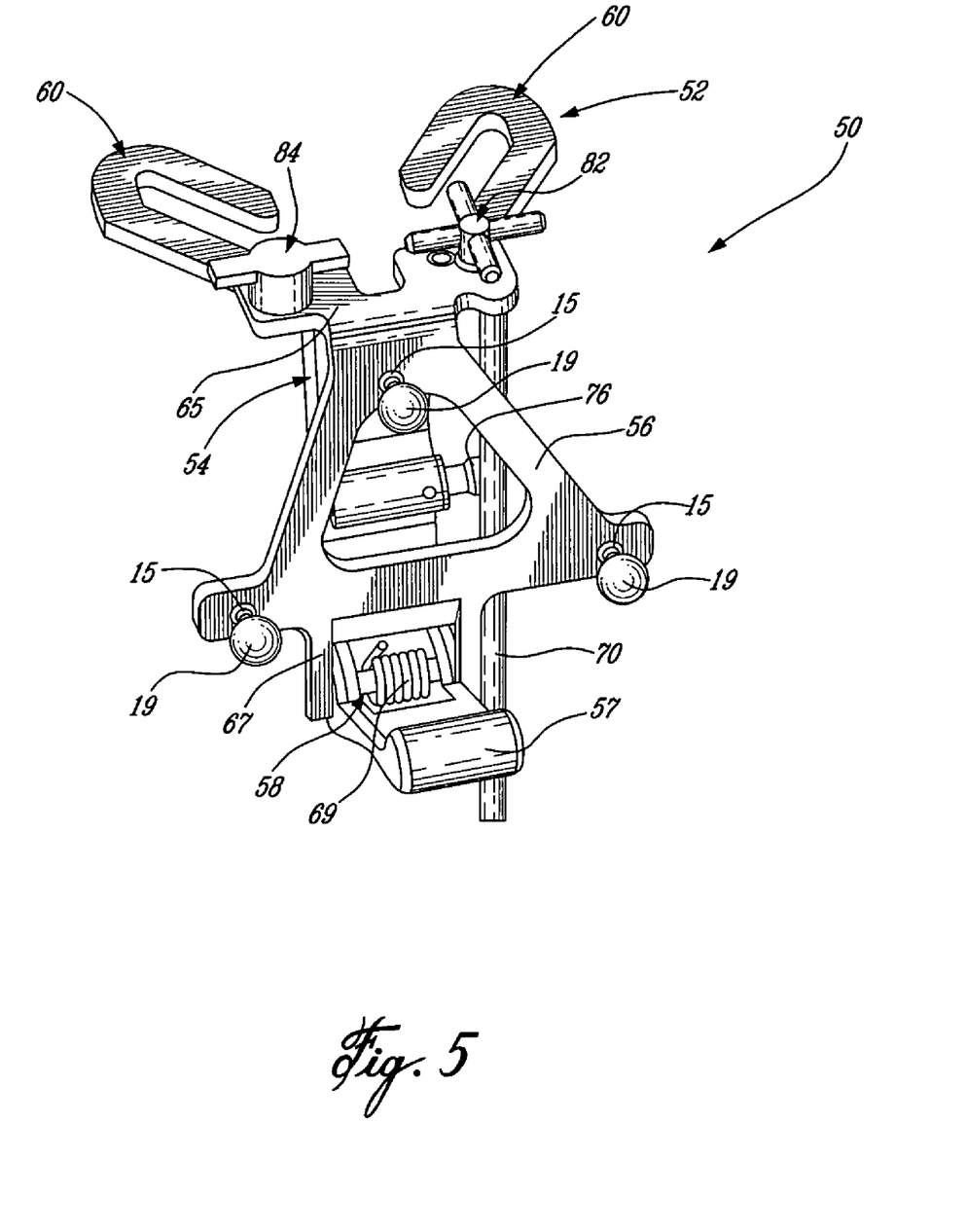
FIG. 5 is a bottom perspective view of the calibration device of FIG. 4.

Referring now to FIGS. 3 to 5, an alternate calibration device 50 similarly permits the determination of the center and axis of rotation of a tracked CAS circular object as well as a reference plane thereon, however is further able to determine the diameter of the circular object. Additionally, the calibration device 50 also permits the calibration of other surgical tools to be used with the CAS system.

The calibration device 50 comprises generally a main body structure 56 to which is engaged at least three support posts 15 that project rearward therefrom. On each post 15 is mounted a detectable element 19, such as those described above which are locatable and trackable by the CAS system, such that the CAS system is able to locate and track the position and orientation in space of the calibration device 50. A substantially U-shaped platform 52 projects in an opposed direction from a lower end 65 of the main body 56, preferably substantially perpendicularly thereto, and includes a pair of spaced apart support elements 60 that form the projecting arms of the U-shaped platform 52 between which a portion (such as the handle/shaft 34 of the impactor 30 described above) of the object to be calibrated may be received. The support elements 60 define upper surfaces 62 on which a planar portion (such as the planar surface 35 described above) of the circular object abut during the calibration thereof. Thus, by knowing the position and orientation of the upper surfaces 62 of the tracked calibration device 50, the CAS system is able to identify and calibrate a plane of the circular object defined by the planar surface thereof. This plane is preferably orthogonal to the axis of rotation of the circular portion of the calibrated object, and the center point of rotation thereof lies within this plane.

A pair of spaced apart pins 66 upwardly project from the platform 52, against which a circumferential edge of the circular object is abutted. A displaceable element 54 is pivotally engaged to an upper end 67 of the main body 56 by a pivot joint 58 located intermediately between an inner end 55 and an outer end 57 of the pivoting element 54. The displaceable element 54 is preferably inwardly biased by a biasing member, such as a torsion spring 69, such that the inner end 55 of the element 54 is biased towards the main body structure 56 and therefore also towards the pins 66. As such, the biased displaceable element 54 serves to retain the circular object being calibrated within the calibration device 10 such that the circumferential edge of the circular object remains abutted against the pins 66 of the device. Further, various circular objects of different sizes can therefore be received and retained within the calibration device 50 for determining the center and axis of rotation thereof. The diameter determining element 54 is preferably generally L-shaped, the outer end 57 thereof at least partially acting to counter balance the pivoting inner end 55.

In use, when the circumferential edge of a circular object, such as the hemispherical impactor head 32 as depicted in FIG. 2 for example, is brought into contact with the upstanding pins 66 of the calibration device 50, the displaceable element 54 is then pivoted towards the circular object such that the inner end 55 thereof is brought into abutting contact with another outer surface of the circular object, generally opposite to that portion of the circumferential edge already in contact with the pins 66 at two corresponding contact points thereon. The inwardly biased element 54 helps retain the circular object within the calibration device to ensure an accurate determination of the center and axis of rotation thereof.

An additional detectable element (not visible), which is located and tracked by the CAS system, is preferably disposed on a displacing portion of the element 54, in addition to the at least three detectable elements 19 fixed to the rear side of the main body 56 of the calibration device. The additional detectable element disposed on the element 54 accordingly permits the CAS system to determine the location of the element 54 when a circular object is installed within the calibration device 50. As such, the CAS system can use the relative position of the element 54 with the known position of the surfaces 62 of the support elements 60, which are used to determine the plane defined by the planar surface of the object, in order to determine the radius and/or diameter of the circular object engaged therebetween. Therefore, when such an additional detectable element or tracker is fixed to the displacing element 54, the user need not have predetermined the diameter of the object for which the center is to be determined, nor input this manually into the CAS system, as this calculation is performed automatically by the CAS system 90 using the calibration device 50.

As best seen in FIG. 4, the calibration device 50 may also include additional fixtures such that it can be used to calibrate other instruments and/or tools for use in conjunction with the CAS system. Particularly, at least two chamfered abutting guides 74 are disposed on the main body structure 56, within which an elongated CAS instrument 70 (such as a tracked pointer, stylus, or the like) can be received. A lower tip 72 of the CAS instrument 70 rests on the platform 61 of the main body 56. The instrument 70 is retained in place within the guides 74 of the calibration device 50 by a retaining element 76, which projects from the displacing element 54 and is therefore also biased towards the main body 56, thereby forcing the instrument 70 to remain in place within the guides 74. The CAS instrument 70 additionally has a tracking member with detectable elements thereon (not shown), and therefore the CAS system is able to calibrate the instrument 70 in reference to the calibration device 50 which has a known position and orientation in space. Accordingly, the central longitudinal axis and the exact location of the tip of the instrument 70 can be determined using the calibration device 50.

As best seen in FIG. 5, the calibration device 50 may also comprise further attachments to permit the calibration of other instruments or tools for use with CAS system. Particularly, connectors 82 and 84 which are provided on a bottom of the calibration device 50, are configured to receive a hollow tubular object such as the drive shaft of a reamer for example. Thus, the reamer drive shaft can be calibrated by fixing it to a suitable one of the connectors 82 and 84. As the position and orientation of the calibration device 50 is known by the CAS system, as is the relative position between the connectors 82 and 84 with the detectable elements 19 of the calibration device, the longitudinal axes of the drive shafts or other instruments engaged to the connectors 82,84, may thus similarly be determined by the CAS system.

Figure 6:
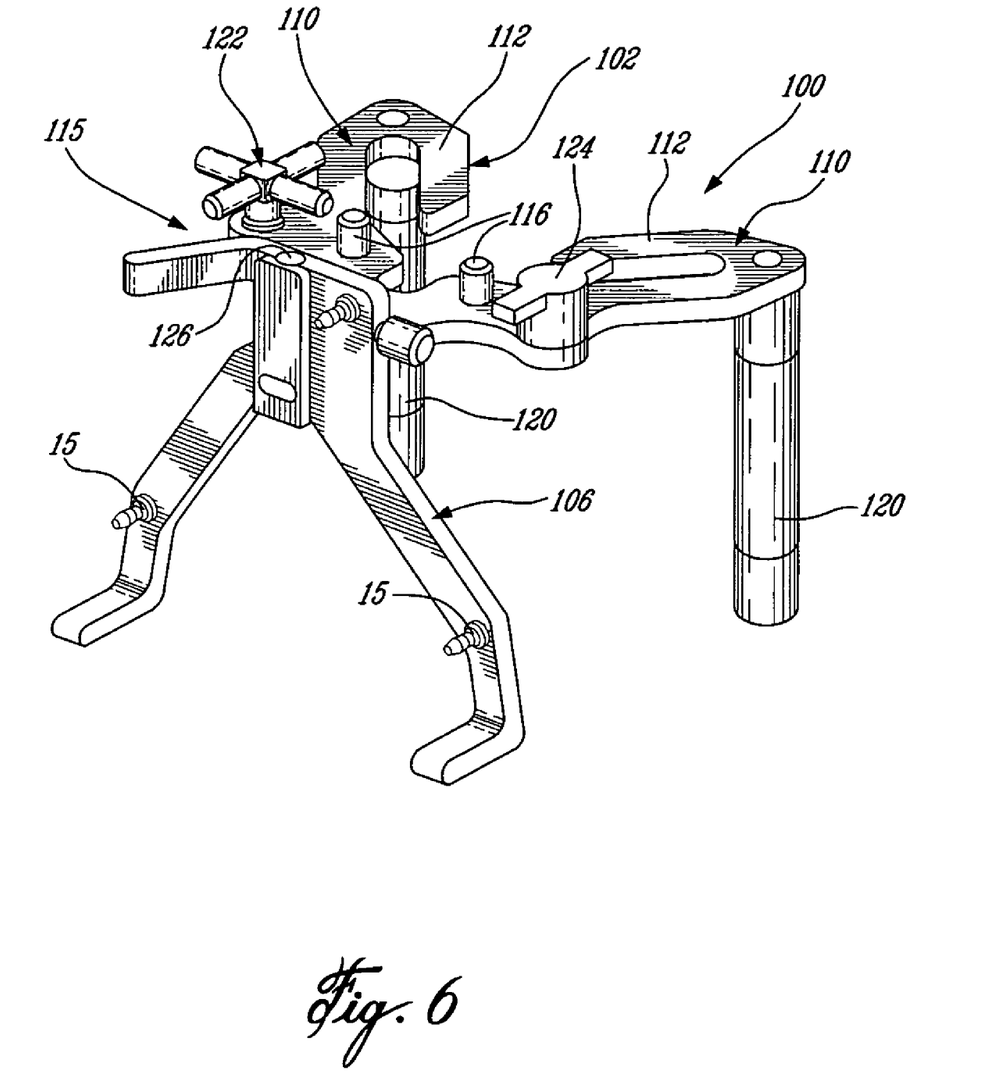
FIG. 6 is a perspective view of a calibration device in accordance with another embodiment of the present invention.

Referring to the alternate embodiment of FIG. 6, the calibration device 100 is similar to the calibration device 50 described above (such as that depicted in FIG. 5), however has no biased pivoting diameter determining element 54. The calibration device 100 includes a main body structure 106 which has at least three support posts 15 that project in a first direction therefrom, and on each of which is mounted a detectable element (not shown in FIG. 6) such as those described above which are locatable and trackable by the CAS system. Thus the CAS system is able to locate and track the position and orientation in space of the calibration device 100. A substantially U-shaped platform 102 projects from one end 115 of the main body 106, preferably substantially perpendicularly thereto, and includes a pair of spaced apart support elements 110 that form the projecting arms of the U-shaped platform 102 between which a portion of the circular surgical object to be calibrated may be received. The support elements 110 each define in upper planar surface 112 which lie in a common plane defined thereby, and on which a planar portion (such as the planar surface 35 of the cup 32 described above) of the circular object is abutted in order to perform the calibration thereof. As the position and orientation of these upper surfaces 112 of the calibration device 100 are known by the CAS system, as they are located in a fixed position relative to the trackable elements on the posts 15, the CAS system is therefore able to identify and calibrate a plane of the circular object defined by the planar surface thereof and abutted against the upper surfaces 112. Two projecting pins 116 extend from the surfaces 112 of the platform 102. A circumferential edge of the circular object being calibrated is thus able to be abutted against these pins 116.

The calibration device 100 further includes a pair of handles 120 which are engaged to the U-shaped platform 102 at the remote ends of the support elements 110 thereof. The handles 120 extend downwardly away from the support elements 110 in a direction opposite to that in which the upstanding pins 116 extend therefrom at the opposite ends of the support elements. The handles 120 are able to be gasped by the user of the calibration device 100, such as to easily permit the manipulation of both the calibration device 100 itself and the surgical object being calibrated when it is disposed in position within the calibration device (i.e. with a planar surface abutted against the surfaces 112 and a circumferential edge abutted against the two pins 116).

The calibration device 100 may also comprise further attachments to permit the calibration of other surgical instruments or tools for use with the CAS system, much as per the calibration device 50 described above. The calibration device 100 as shown in FIG. 6 therefore also includes connectors 122 and 124 located on a base portion of the platform 102 proximate the main body 106, which are configured to receive a hollow tubular object thereover, such as the drive shaft of a reamer for example, in order to permit this additional surgical implement to be calibrated by the device 100. Several other various projections and/or recesses may be provided, such as the recess 126 and the post projection 128 disposed respectively in and on the main body 106 of the device, such as to permit the calibration of other surgical tools used in conjunction with the CAS system.

In use, the calibration device 100 functions much as per the previously described embodiments, such as to permit the determination of at least the center point of the circular surgical objection being calibrated, and also preferably a plane in which the center point lies and the axis of rotation of the circular object.

The above description is meant to be exemplary only, and one skilled in the art will recognize that changes may be made to the embodiments described without department from the scope of the invention disclosed. Still other modifications which fall within the scope of the present invention will be apparent to those skilled in the art, in light of a review of this disclosure, and such modifications are intended to fall within the appended claims.

The invention claimed is:

1. A method of calibrating an object using a computer tracking system, the object having a planar portion and a circular portion at least partially opposite said planar portion, the circular portion having a diameter, the method comprising the steps of:
   providing a calibration device having a tracking member thereon which is located and tracked in three dimensional space by the computer tracking system;
   determining a position and orientation of at least two object contacting portions of the calibration device using the computer tracking system;
   abutting said object contacting portions against said circumferential edge of said circular portion; while abutting a planar reference surface of the calibration device against said planar portion of the object;
   determining spatial coordinates of at least two points on a circumferential edge of said circular portion of the object which are in contact with said object contacting portions;
   calculating the center point of said circular portion using said spatial coordinates of said at least two points and a geometric parameter representative of the diameter of said circular portion; and
   using the calculated center point to calibrate the object using the computer tracking system.

2. The method as defined in claim 1, further comprising predetermining the geometric parameter representative of the diameter and inputting said predetermined geometric parameter into said computer tracking system.

3. The method as defined in claim 1, further comprising using the computer tracking system to determine the geometric parameter representative of the diameter of said circular portion.

4. The method as defined in claim 3, wherein the step of determining the geometric parameter includes measuring a radius of the circular portion.

5. The method as defined in claim 1, wherein the step of calculating includes using the computer tracking system to determine an intersection point between two imaginary lines originating at said two points, each imaginary line having a length equal to half of said diameter, said intersection point corresponding to said center point.

6. The method as defined in claim 1, further comprising determining a position and orientation of a plane defined by the planar portion of the object using the computer tracking system, the center point of the circular portion lying in said plane.

7. A method of calibrating an object for use with a computer tracking system, the object having at least a circular portion defining a diameter and a planar portion at least partially opposite the circular portion, the method comprising:

providing a calibration device having thereon a tracking member which is located and tracked in three dimensional space by the computer tracking system, the calibration device including at least two object contacting portions located known distances from said tracking member and apart from each other;

abutting said at least two object contacting portions against a circumferential edge of said circular portion such that said at least two object contacting portions contact said circumferential edge at two points thereon, and abutting a planar reference surface of the calibration device against the planar portion of the object;

using the computer tracking system to determine spatial coordinates of said two points on said circumferential edge of the circular portion;

calculating a center point of said circular portion using said two points on said circumferential edge and a geometric parameter representative of the diameter of the circular portion; and using the calculated center point to calibrate the object using the computer tracking system.

8. The method as defined in claim 7, further comprising predetermining the diameter of the circular portion of the object and inputting said predetermined diameter into said computer tracking system.

9. The method as defined in claim 7, further comprising determining the diameter of the circular portion using said calibration device.

10. The method as defined in claim 9, further comprising positioning the circular portion between a first fixed surface of the calibration device and a second surface of a displaceable portion of the calibration device, the displaceable portion having thereon a tracking member which is located and tracked by the computer tracking system.

11. The method as defined in claim 7, wherein the step of calculating includes determining an intersection point between two imaginary lines originating at said two points, each imaginary line having a length equal to half of said diameter, said intersection point corresponding to said center point.

12. The method as defined in claim 7, further comprising determining a position and orientation of a plane defined by the planar portion on the object, the center point of the circular portion lying in said plane.

13. A system for calibrating an object having a circular portion and a planar portion at least partially opposite the circular portion, the system comprising:
  a computer tracking system operable to locate and track in three dimensional space a plurality of tracking members communicable with the computer tracking system;
  a calibration device including at least one of said tracking members thereon, the calibration device having at least one object receiving surface thereon for abutment with the circular portion of the object, wherein said object contacting portions against said circumferential edge of said circuit portion and abutment a planar reference surface of the calibration device against said planar portion of the object; and
  a calculation module of the computer tracking system, said calculation algorithm being operable to calculate at least one of spatial coordinates of a center point of the circular portion and a geometric parameter of the circular portion representative of a diameter thereof.

14. The system as defined in claim 13, wherein the at least one object receiving surface of the calibration device includes at least two object contacting portions spaced apart to receive a circumferential edge of the circular portion of the object therebetween, the object contacting portions being located known distances from said tracking member and each other, such that their position and orientation in three dimensional space is determined by the computer tracking system.

15. The system as defined in claim 13, wherein said planar reference surface of the calibration device is disposed in a known position and orientation relative to said object contacting portions, the computer tracking system being operable to determine the position and orientation of a plane defined by said planar surface.

16. The system as defined in claim 15, wherein the calculated center point of the circular portion lies within said plane.

17. The system as defined in claim 15, wherein the calibration device includes a displaceable portion having at least another of said tracking members thereon, the displaceable portion being displaceable towards said planar surface of the calibration device to abut an outer surface of the circular portion, thereby retaining the object between said displaceable portion and said planar surface.

18. The system as defined in claim 17, wherein the displaceable portion is pivotable relative to a main body of the calibration device fixed relative to said planar surface.

19. The system as defined in claim 18, wherein the displaceable portion is biased towards said planar surface to maintain abutting contact with said object when disposed there within.

20. A calibration device for calibrating at least a circular portion of an object using a computer tracking system, the circular portion having at least a curved circumferential edge and an intersecting planar face, the calibration device comprising:
  a main body having a platform portion defining at least a first planar surface thereon, the first planar surface being adapted for receiving the planar face of the circular portion abutted there against, and at least two elements projecting from said first planar surface, said elements being spaced apart to receive the curved circumferential edge of the circular portion there between when said curved circumferential edge is abutted against said elements;
  a tracking member fixed to said main body, the tracking member being locatable and trackable in three dimensional space by the computer tracking system; and
  said first planar surface and each of the elements being located a known distance from said tracking member such that their position and orientation in three dimensional space is determinable by the computer tracking system, and thus the spatial coordinates of points on the curved circumferential edge and the planar face of the circular portion which are abutted against said first planar surface and said elements are accordingly determinable by the computer tracking system.

21. The calibration device as defined in claim 20, wherein said platform portion of said main body is substantially U-shaped.

22. The calibration device as defined in claim 20, wherein at least one handle extends from said main body for manipulation of the calibration device.

23. The calibration device as defined in claim 22, wherein said at least one handle includes a pair of handles, each one of said pair of handles extending from a remote end of said platform portion.

24. The calibration device as defined in claim 20, wherein at least one connector is located on said main body for engagement with another object, such that said another object is calibrated using said calibration device.

25. The calibration device as defined in claim 20, further comprising a displaceable portion having at least another of said tracking members thereon, the displaceable portion being engaged with said main body and displaceable towards said first planar surface to abut an outer surface of the circular portion of the object received within the calibration device, thereby retaining the object between said displaceable portion and said first planar surface.

26. The calibration device as defined in claim 25, wherein the displaceable portion is pivotable relative to the main body.

27. The system as defined in claim 26, wherein the displaceable portion is biased towards said first planar surface such as to maintain abutting contact with said object when received within the calibration device.

* * * * *